(12) United States Patent
Chau

(10) Patent No.: US 11,291,628 B2
(45) Date of Patent: Apr. 5, 2022

(54) CHEWABLE PHARMACEUTICAL PRODUCT FOR DELIVERY OF COLESEVELAM HYDROCHLORIDE

(71) Applicant: Cosette Pharmaceuticals, Inc., Bridgewater, NJ (US)

(72) Inventor: Tommy L. Chau, Ashburn, VA (US)

(73) Assignee: Cosette Pharmaceuticals, Inc., Bridgewater, NJ (US)

( * ) Notice: Subject to any disclaimer, the term of this patent is extended or adjusted under 35 U.S.C. 154(b) by 296 days.

(21) Appl. No.: 15/215,804

(22) Filed: Jul. 21, 2016

(65) Prior Publication Data

US 2018/0021255 A1 Jan. 25, 2018

(51) Int. Cl.
| | | |
|---|---|---|
| *A61K 9/00* | (2006.01) | |
| *A61K 31/785* | (2006.01) | |
| *A61K 9/14* | (2006.01) | |
| *A61P 3/06* | (2006.01) | |

(52) U.S. Cl.
CPC ............ *A61K 9/0056* (2013.01); *A61K 9/145* (2013.01); *A61K 31/785* (2013.01); *A61P 3/06* (2018.01)

(58) Field of Classification Search
CPC ....... A61K 9/0056; A61K 31/785; A23G 3/00
See application file for complete search history.

(56) References Cited

U.S. PATENT DOCUMENTS

| | | | |
|---|---|---|---|
| 5,637,313 A | 6/1997 | Chau | |
| 6,482,465 B1 | 11/2002 | Cherukuri | |
| 6,517,886 B1 | 2/2003 | Chau | |
| 2008/0008742 A1 * | 1/2008 | Cherukuri | ............ A61K 9/0056 424/439 |
| 2009/0232916 A1 * | 9/2009 | Shulman | .................. A21D 2/02 424/752 |
| 2010/0061968 A1 * | 3/2010 | Lines | ................... A61K 31/352 424/93.51 |

FOREIGN PATENT DOCUMENTS

WO     WO-0110236 A1 * 2/2001 ............... A23G 3/42

OTHER PUBLICATIONS

Goldberg, R. et al., "Efficacy and safety of clesevelam in patients with type 2 diabetes Mellitus and inadequate glycemic control receiving insulin-based therapy", Arch Intern Med, 2008, vol. 168, No. 14, pp. 1531-1540.*

Heume, M. et al., "Versatility of maltitol in different forms as a sugar substitute", Advances in Sweeteners, 1996 (edited by Grenby T.H.), Springer, pp. 85-108.*

* cited by examiner

*Primary Examiner* — Gina C Justice
(74) *Attorney, Agent, or Firm* — Dentons Cohen & Grigsby P.C.

(57) ABSTRACT

A chewable pharmaceutical product comprises a matrix comprising: a binder, a bulking agent, a lubricant, a humectant, an emulsifier, and optionally a flavoring, wherein the binder comprises one or more maltitol syrups, which are present in the pharmaceutical product in an amount in the range of 60-70% by weight; and colesevelam hydrochloride.

17 Claims, No Drawings

CHEWABLE PHARMACEUTICAL PRODUCT FOR DELIVERY OF COLESEVELAM HYDROCHLORIDE

TECHNICAL FIELD

The present disclosure generally relates to a chewable pharmaceutical product for delivery of colesevelam hydrochloride.

BACKGROUND

Colesevelam hydrochloride (commercially known as WECHOL®) is a non-absorbed, polymeric, lipid-lowering and glucose-lowering agent intended for oral administration. Indications of colesevelam hydrochloride include reducing elevated low-density lipoprotein cholesterol (LDL-C) in adults with hyperlipidemia and improving glycemic control in adults with type 2 diabetes mellitus.

At least about 16 million Americans have type 2 diabetes. Individuals afflicted with type 2 and type 1 diabetes have elevated blood sugar levels due to problems with either the amount of or action of insulin, which regulates the body's handling of glucose. In type 1 diabetes, the pancreas is unable to respond normally to blood sugar levels by secreting insulin. In type 2 diabetes, the more common form, the liver and peripheral tissues may be less responsive to insulin. In later stages of type 2 diabetes, the pancreas may also secrete inadequate amounts of insulin for proper blood sugar control. Diabetic individuals who control blood glucose levels can substantially reduce the risk of developing vascular complications of diabetes, including, but not limited, to diabetic retinopathy (a condition which leads to blindness), diabetic nephropathy, diabetic neuropathy, and atherosclerosis.

The American Diabetes Association has recommended that patients with type 2 diabetes be treated to a goal of glycosylated hemoglobin A (HbA1c) of <7%, the level at which clinical trials have demonstrated fewer long-term microvascular complications. From the Third National Health and Nutrition Examination Survey data, it appears that only about 40% of patients with type 2 diabetes achieve this goal.

Taking care of patients with diabetes mellitus and its complications is estimated to cost more than $132 billion each year. Much of the personal and economic burden related to the care of diabetic patients stems from inadequate glycemic control. Studies have demonstrated that glycemic control in the majority of patients with type 2 diabetes is inadequate. The position statement of the ADA recommends that all patients with type 2 diabetes be treated with diet, exercise, and when necessary, with medication to bring their HbA1c levels to below a threshold of 7%. An epidemiological analysis of the UK Prospective Diabetes Study data demonstrated an approximate 14% reduction in all-cause mortality and myocardial infarction for every 1% reduction in HbA1c. Furthermore, it is estimated that there is a 15%-30% reduction in the risk of microvascular complications for each 1% reduction in HbA1c.

The recommended dose of WELCHOL is 3.75 grams daily. WELCHOL is available in tablet form (625 mg colesevelam hydrochloride/tablet) and in packets of granules for oral suspensions (3.75 or 1.875 gram colesevelam hydrochloride/packet). In order for a patient to ingest the recommended dose in tablet form, the patient needs to consume 6 tablets, whose size can cause difficulty in swallowing for some patients. In order for a patient to ingest the recommended dose in granule form, the patient needs to mix the granules into 4-8 ounces of water, fruit juice, or diet soft drinks.

There is a desire to deliver colesevelam hydrochloride in dosage forms that are easy to handle and ingest.

SUMMARY

Chewable pharmaceutical products that deliver colesevelam hydrochloride are provided. Methods of making and using the same are also provided.

A first aspect is a chewable pharmaceutical product comprising: a matrix comprising: a binder, a bulking agent, a lubricant, a humectant, an emulsifier, and optionally one or more of a flavoring, a coloring, and an antioxidant, wherein the binder comprises one or more maltitol syrups that are present in the pharmaceutical product in an amount in the range of 60-70% by weight; and colesevelam hydrochloride.

The colesevelam hydrochloride may present in a dosage of 3.75 grams±10%. The chewable pharmaceutical product delivering 3.75 grams±10% of colesevelam hydrochloride may be present in the form of a bar having a unit weight of 30 g±10%. Alternatively, the colesevelam hydrochloride is present in a dosage of 625 milligrams±10%. The chewable pharmaceutical product delivering 625 milligrams±10% colesevelam hydrochloride may be present in the form of a chew having a unit weight of 5 g±10%.

The maltitol syrup may comprise one or more maltitol syrups, which in combination have an effective solids content in the range of 81.5-83.3%.

The bulking agent may be sugar-free, comprising one or more of: sorbitol, mannitol, xylitol, lactitol, maltitol, isomalt, erythritol, polydextrose, maltodextrin, gelatin, gum acacia, gum Arabic, carrageenan, locust bean gum, and guar gum. The lubricant may comprise palm oil, cocoa butter, sunflower oil, or combinations thereof. The emulsifier may comprise: lecithin, distilled monoglycerides, mono-diglycerides, distilled propylene glycol monoester, succinylated monoglycerides, glyceryl monostearate, diacetyl tartaric acid esters of mono-diglycerides, glycerol lacto palmitates, polyglycerol esters, stearol lactylates, sorbitan esters of polysorbates, or combinations thereof. The humectant may comprise: glycerin, propylene glycol, or combinations thereof. The flavoring may comprise: chocolate flavor, vanilla flavor, strawberry flavor, caramel flavor, or combinations thereof.

The chewable pharmaceutical product may comprise by weight:
  (a) colesevelam hydrochloride in an amount of 3.75 grams±10%;
  (b) maltitol syrup as the binder in an amount in the range of 63-66%;
  (c) one or more of: maltodextrin and gum acacia as the bulking agent totaling an amount in the range of 5-15%;
  (d) palm oil as the lubricant in an amount in the range of 1.5-6%;
  (e) glycerin as the humectant in an amount in the range of 1-3%;
  (f) lecithin as the emulsifier in an amount in the range of 1-2%;
  (g) a flavoring in an amount in the range of 0.01-6%; and
  (h) optionally one or more of a powdered sweetener, a coloring, and an antioxidant.

The chewable pharmaceutical product may comprise by weight:
(a) colesevelam hydrochloride in an amount of 12.5%;
(b) maltitol solids in an amount in the range of 52-54%;
(c) one or more of: maltodextrin and gum acacia as the bulking agent totaling an amount in the range of 5-15%;
(d) palm oil as the lubricant in an amount in the range of 1.5-6%;
(e) glycerin as the humectant in an amount in the range of 1-3%;
(f) lecithin as the emulsifier in an amount in the range of 1-2%;
(g) a flavoring in an amount in the range of 0.01-6%;
(h) water in an amount in the range of 11.5-12.5% and
(i) optionally one or more of a powdered sweetener, a coloring, and an antioxidant;
wherein ingredients (a)-(i) total 100%.

Another aspect is a method of delivering colesevelam hydrochloride, which comprises: administering any chewable pharmaceutical product disclosed herein to a patient in need of glycemic control or lipid-lowering. The chewable pharmaceutical product may be ingested once per day.

Another aspect is a method of making a chewable pharmaceutical product for delivery of colesevelam hydrochloride, which comprises:
(i) heating an amount of one or more maltitol syrups to a temperature of in the range of 120-160° F.;
(ii) melting a lubricant;
(iii) blending dry ingredients in a mixer, the dry ingredients comprising: at least colesevelam hydrochloride and a bulking agent,
(iv) adding the maltitol syrups, the lubricant, a humectant, and an emulsifier to the dry ingredients in the mixer;
(v) optionally adding one or more of a flavoring, coloring, and an antioxidant to the mixture;
(vi) mixing all of the ingredients until substantially uniform to form an active-ingredient-containing matrix;
(vii) extruding the active-ingredient-containing matrix and then cutting to form the chewable pharmaceutical product,
wherein the amount of the one or more maltitol syrups in the chewable pharmaceutical product is in the range of 60-70% by;
(viii) packaging the chewable pharmaceutical product.
Extruding may occur at a temperature of 40° C.±10° C.

DETAILED DESCRIPTION

Chewable pharmaceutical products for delivery of colesevelam hydrochloride comprise: a matrix and colesevelam hydrochloride. The matrix comprises: a binder, a bulking agent, a lubricant, a humectant, an emulsifier, and optionally a flavoring, wherein the binder comprises one or more maltitol syrups. In the present disclosure the maltitol syrup(s) are present in the chewable pharmaceutical product in an amount in the range of 60-70% by weight. In a detailed embodiment, the colesevelam hydrochloride is present in a dosage of 3.75 grams±10%. The chewable pharmaceutical products may be in the form of a bar having a unit weight of 30 g±10%. In another detailed embodiment, the colesevelam hydrochloride is present in a dosage of 625 milligrams±10% and the product is in the form of a chew having a unit weight of 5 g±10%.

Before describing several exemplary embodiments of the invention, it is to be understood that the invention is not limited to the details of construction or process steps set forth in the following description. The invention is capable of other embodiments and of being practiced or being carried out in various ways.

Dosage Forms

Chewable pharmaceutical products as dosage forms include a matrix and a colesevelam hydrochloride.

Colesevelam hydrochloride is a highly cross-linked polymer and is insoluble in most aqueous and organic solvents. The activity of colesevelam hydrochloride is not dependent on its dissolution or absorption since colesevelam hydrochloride is not absorbed in vivo. Colesevelam hydrochloride binds bile acids in the intestine, impeding their reabsorption.

Colesevelam hydrochloride is a tetrapolymer of allyamine, N-decylallyamine, N-(6-trimethylammoniumhexyl) allylamine and N,N'-diallyl-1,3-diamino-2-hydroxypropane. (CAS number: 182815-44-7).

The molecular formula of colesevelam hydrochloride is:

$$(C_3H_8NCl)_2(C_9H_{20}N_2OCl_2)_1(C_{13}H_{28}NCl)_7$$
$$(C_{12}H_{28}N_2Cl_2)_6$$

The matrix comprises: a binder, a bulking agent, a lubricant, a humectant, an emulsifier, and optionally one or more of a flavoring, a coloring, and an antioxidant. The binder comprises one or more maltitol syrups. The maltitol syrups may have differing solids contents. Commercially available maltitol syrups generally have solids content of 75% or 85%. Mixtures of maltitol syrups may be used in order to meet desired solids/moisture content. In a detailed embodiment, the binder comprises a first maltitol syrup having a solids content of 85% and a second maltitol syrup having a solids content of 75%. A ratio of the first maltitol syrup to the second maltitol syrup, where the first maltitol syrup has a higher solids content than the second maltitol syrup, may be in the range of 2:1 to 4:1 or even 2.5:1 to 3.3:1. The maltitol syrup may comprise one or more maltitol syrups, which in combination have an effective solids content in the range of 81.5-83.3% (and a corresponding effective water content in the range of 16.7-18.5).

The bulking agent may comprise pharmaceutically acceptable bulking agents, which provide volume and mass to the bar without impacting the active ingredient. Preferably the bulking agent is sugar-free. For example, the bulking agent may comprise one or more of: maltodextrin, gelatin, gum acacia, gum Arabic, carrageenan, locust bean gum, and guar gum. Other sugarless ingredients include but are not limited to: sorbitol, mannitol, xylitol, lactitol, maltitol, isomalt, erythritol, and polydextrose.

The lubricant may comprise any edible oil. Exemplary lubricants include but are not limited to: palm oil, cocoa butter, sunflower oil, or combinations thereof. Exemplary emulsifiers include but are not limited to: lecithin, distilled monoglycerides, mono-diglycerides, distilled propylene glycol monoester, succinylated monoglycerides, glyceryl monostearate, diacetyl tartaric acid esters of mono-diglycerides, glycerol lacto palmitates, polyglycerol esters, stearol lactylates, sorbitan esters of polysorbates, or combinations thereof. Exemplary humectants include but are not limited to: glycerin and/or propylene glycol. Preferred flavorings include but are not limited to: chocolate, vanilla, strawberry, caramel, and combinations thereof.

Method of Making

The chewable pharmaceutical products are made as follows. A maltitol syrup is heated to a temperature in the range of 120-160° F. Any solid-form lubricants are melted. All dry ingredients are blended in a mixer, the dry ingredients generally comprising: colesevelam hydrochloride raw material, a bulking agent, and any colorings or flavors in solid/ powder form. The heated maltitol syrup and lubricant along with liquid ingredients, e.g., a humectant and an emulsifier are all added to the dry ingredients in the mixer. At this point, one or more flavorings, colorings, or antioxidants are added to the mixture. All of the ingredients are mixed until substantially uniform to form an active-ingredient-containing matrix. The active-ingredient-containing matrix is extruded, which may be at a temperature of 40° C.±10° C. The range of temperature may vary according to application. In some applications, a variation of ±10° C. is desired, whereas in other applications, variations of ±5° C. may be desired. The extrudate is then cut to form the chewable pharmaceutical product, which is then packaged. The products may be in any suitable form for packaging and distribution to consumers, including but not limited to bars and chews.

EXAMPLE

Example 1

For the purposes of organoleptic testing, colesevelam hydrochloride soft chews were prepared as a single unit formulation consisting of approximately 625 mg of colesevelam hydrochloride as the active ingredient. The general composition of the soft chews is summarized in Table 1. The excipients used in colesevelam hydrochloride soft chews were food grade. Each colesevelam hydrochloride soft chew was individually wrapped.

TABLE 1

Colesevelam hydrochloride Soft Chews

| Ingredient | Amount (%) | Function |
| --- | --- | --- |
| Colesevelam hydrochloride | 12.5% | Active ingredient |
| Maltitol syrup 85% solids | 63-66% | Binder |
| Maltodextrin | 5.08-6.50% | Bulking agent |
| Gum Acacia | 0-6.4% | Bulking agent |
| Palm Oil | 5.5% | Lubricant |
| Glycerin | 2% | Humectant |
| Lecithin | 1-2% | Emulsifier |
| Flavors | 0.01-5.71% | Flavoring |
| Sucralose | 0.08-0.11% | Intense Sweetener |

Maltitol syrup was heated to approximately 120° F. All of the powder ingredients (colesevelam hydrochloride, maltodextrin, gum acacia, sucralose, and any colorings or flavors in solid/powder form) were blended together in a mixer for at least 3 minutes. The maltitol syrup, glycerin, colorings (if applicable), lecithin, melted palm oil and rosemary extract (as an antioxidant in an amount of 0.01 wt. %) were added to the mixer. Liquid flavors were added next and mixed for, at least, an additional 7 minutes. The resultant mass of an active-ingredient-containing matrix was removed from the mixer, placed into a plastic bag, manually rolled flat and cut into individual 5 gram pieces. Each piece was wrapped into a silver foil wrap.

Example 2

Chocolate-flavored soft bars were prepared, the composition of which is provided in Table 2.

TABLE 2

Soft Bars

| Ingredient | Example 2 Amount (%) |
| --- | --- |
| Maltitol syrup 85% Solids$^{(A)}$ (Lycasin 85/55) | 45.00% |
| Maltitol syrup 75% Solids$^{(B)}$ (Maltisweet 3145) | 20.00% |
| Colesevelam hydrochloride raw material$^{(C)}$ | 13.13% |
| Maltodextrin (Maltrin M180) | 6.97% |
| Alkalized Cocoa | 6.50% |
| Natural Vanilla Type Flavor (FONATECH ® Vanilla 926.0701U) | 2.00% |
| Natural & Artificial Chocolate Flavor (Chocolate 826.2208U) | 1.80% |
| High Melting Palm Oil (Revel A) | 1.50% |
| Palm Oil (Cisao 83-12) | 1.00% |
| Glycerin | 1.00% |
| Soy Lecithin | 1.00% |
| Sucralose | 0.09% |
| Natural Rosemary Extract Flavor (Herbalox Type O 41-19-01) | 0.01% |
| TOTAL | 100.00% |

$^{(A)}$85% solids maltitol syrup nominally comprises about 15 wt.-% water and about 85 wt.-% of maltitol solids, which is substantially a mixture of maltitol, sorbitol, and polyitols.
$^{(B)}$75% solids maltitol syrup nominally comprises about 25 wt.-% water and about 75 wt.-% of maltitol solids, which is substantially a mixture of maltitol, sorbitol, and polyitols.
$^{(C)}$Colesevelam hydrochloride supplied as a raw material contains generally 95% active ingredient and 5% molecular water.

Accounting for the adjustments based on (A)-(C), the bars contained 12.38 wt.-% water, 12.5 wt.-% colesevelam hydrochloride, and 53.25 wt.-% maltitol solids. The effective solids content of the maltitol syrups in combination was 81.92 wt.-%, and the effective water content was 18.08 wt.-%.

The maltitol syrups were heated to 120° F.-160° F. All of the dry/powder ingredients (colesevelam hydrochloride raw material, maltodextrin, gum acacia, sucralose, and any colorings or flavors in solid/powder form) were blended together in a mixer for at least 3 minutes. The maltitol syrup, glycerin, colorings (if applicable), lecithin, melted palm oil and rosemary extract (as an antioxidant in an amount of 0.01 wt. %) were added to the mixer. Liquid flavors were added next and mixed for, at least, an additional 7 minutes. The resultant mass of an active-ingredient-containing matrix was conveyed from the mixer to an extruder, which was heated. The active-ingredient-containing matrix was extruded at 40° C.±5° C., rolled flat, and cut into 30 gram bars. Each bar was wrapped.

Example 3

Strawberry-flavored soft bars were prepared as described in Example 2, the composition of which is provided in Table 3.

TABLE 3

Soft Bars

| Ingredient | Example 3 Amount (%) |
| --- | --- |
| Maltitol syrup 85% Solids$^{(A)}$ (Lycasin 85/55) | 45.00% |
| Maltitol syrup 75% Solids$^{(B)}$ (Maltisweet 3145) | 20.00% |
| Colesevelam hydrochloride raw material$^{(C)}$ | 13.13% |

TABLE 3-continued

Soft Bars

| Ingredient | Example 3 Amount (%) |
|---|---|
| Maltodextrin (Maltrin M180) | 11.03% |
| Gum Acacia (InstantGum BB) | 4.00% |
| Palm Oil (Cisao 83-12) | 1.50% |
| High Melting Palm Oil (Revel A) | 1.00% |
| Natural & Artificial Strawberry Cheesecake Type Flavor (Strawberry Cheesecake 915.2224U) | 2.00% |
| Glycerin | 1.00% |
| Soy Lecithin | 1.00% |
| Citric Acid | 0.25% |
| Sucralose | 0.07% |
| FD&C Red #40 Powder | 0.01% |
| Natural Rosemary Extract Flavor (Herbalox Type O 41-19-01) | 0.01% |
| TOTAL | 100.00% |

(A) 85% solids maltitol syrup nominally comprises about 15 wt.-% water and about 85 wt.-% of maltitol solids, which is substantially a mixture of maltitol, sorbitol, and polyitols.
(B) 75% solids maltitol syrup nominally comprises about 25 wt.-% water and about 75 wt.-% of maltitol solids, which is substantially a mixture of maltitol, sorbitol, and polyitols.
(C) Colesevelam hydrochloride supplied as a raw material contains generally 95% active ingredient and 5% molecular water.

Accounting for the adjustments based on (A)-(C), the bars contained 12.38 wt.-% water, 12.5 wt.-% colesevelam hydrochloride, and 53.25 wt.-% maltitol solids. The effective solids content of the maltitol syrups in combination was 81.92 wt.-%, and the effective water content was 18.08 wt.-%.

Example 4

Caramel-flavored soft bars were prepared as described in Example 2, the composition of which is provided in Table 4.

TABLE 4

Soft Bars

| Ingredient | Example 4 Amount (%) |
|---|---|
| Maltitol syrup 85% Solids$^{(A)}$ (Lycasin 85/55) | 50.00% |
| Maltitol syrup 75% Solids$^{(B)}$ (Maltisweet 3145) | 15.00% |
| Colesevelam hydrochloride raw material$^{(C)}$ | 13.13% |
| Maltodextrin (Maltrin M180) | 9.89% |
| Natural Vanilla Type Flavor (FONATECH ® Vanilla 926.0701U) | 1.70% |
| Palm Oil (Cisao 83-12) | 1.50% |
| High Melting Palm Oil (Revel A) | 1.00% |
| Caramel Natural WONF 822.0251U | 1.50% |
| Glycerin | 1.00% |
| Soy Lecithin | 1.00% |
| Gum Acacia (InstantGum BB) | 4.00% |
| Sucralose | 0.07% |
| Caramel Color Liquid # 108 | 0.20% |
| Natural Rosemary Extract Flavor (Herbalox Type O 41-19-01) | 0.01% |
| TOTAL | 100.00% |

(A) 85% solids maltitol syrup nominally comprises about 15 wt.-% water and about 85 wt.-% of maltitol solids, which is substantially a mixture of maltitol, sorbitol, and polyitols.
(B) 75% solids maltitol syrup nominally comprises about 25 wt.-% water and about 75 wt.-% of maltitol solids, which is substantially a mixture of maltitol, sorbitol, and polyitols.
(C) Colesevelam hydrochloride supplied as a raw material contains generally 95% active ingredient and 5% molecular water. The effective solids content of the maltitol syrups in combination was 82.69 wt.-%, and the effective water content was 17.31 wt.-%.

Accounting for the adjustments based on (A)-(C), the bars contained 11.88 wt.-% water, 12.5 wt.-% colesevelam hydrochloride, and 53.75 wt.-% maltitol solids.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein provided a description with reference to particular embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents.

What is claimed is:

1. A chewable pharmaceutical product comprising:
    a matrix comprising: a binder, a bulking agent, a lubricant, a humectant, an emulsifier, and optionally one or more of a flavoring, a coloring, and an antioxidant, wherein the binder comprises one or more maltitol syrups that are present in the pharmaceutical product in an amount in the range of 60-70% by weight; and
    colesevelam hydrochloride wherein the maltitol syrup comprises two maltitol syrups: a first maltitol syrup having a higher solids content than a second maltitol syrup, which are present in a weight ratio (first maltitol syrup:second maltitol syrup) of from 2:1 to 4:1, which in combination, have an effective solids content in the range of 81.5-83.3%.

2. The chewable pharmaceutical product of claim 1, wherein the colesevelam hydrochloride is present in a dosage of 3.75 grams±10%.

3. The chewable pharmaceutical product of claim 2 in the form of a bar having a unit weight of 30 g±10%.

4. The chewable pharmaceutical product of claim 1, wherein the colesevelam hydrochloride is present in a dosage of 625 milligrams±10%.

5. The chewable pharmaceutical product of claim 4 in the form of a chew having a unit weight of 5 g±10%.

6. The chewable pharmaceutical product of claim 1, wherein the bulking agent is sugar-free, comprising one or more of: sorbitol, mannitol, xylitol, lactitol, maltitol, isomalt, erythritol, polydextrose, maltodextrin, gelatin, gum acacia, carrageenan, locust bean gum, and guar gum.

7. The chewable pharmaceutical product of claim 1, wherein the lubricant comprises palm oil, cocoa butter, sunflower oil, or combinations thereof.

8. The chewable pharmaceutical product of claim 1, wherein the emulsifier comprises: lecithin, distilled monoglycerides, mono-diglycerides, distilled propylene glycol monoester, succinylated monoglycerides, glyceryl monostearate, diacetyl tartaric acid esters of mono-diglycerides, glycerol lacto palmitates, polyglycerol esters, stearol lactylates, sorbitan esters of polysorbates, or combinations thereof.

9. The chewable pharmaceutical product of claim 1, wherein the humectant comprises: glycerin, propylene glycol, or combinations thereof.

10. The chewable pharmaceutical product of claim 1, comprising the flavoring that comprises: chocolate flavor, vanilla flavor, strawberry flavor, caramel flavor, or combinations thereof.

11. The chewable pharmaceutical product of claim 1 comprising by weight of the pharmaceutical product:
(a) colesevelam hydrochloride in an amount of 3.75 grams±10%;
(b) maltitol syrup as the binder in an amount in the range of 63-66%;
(c) one or more of: maltodextrin and gum acacia as the bulking agent totaling an amount in the range of 5-15%;
(d) palm oil as the lubricant in an amount in the range of 1.5-6%;
(e) glycerin as the humectant in an amount in the range of 1-3%;
(f) lecithin as the emulsifier in an amount in the range of 1-2%;
(g) a flavoring in an amount in the range of 0.01-6%; and
(h) optionally one or more of a powdered sweetener, a coloring, and an antioxidant.

12. The chewable pharmaceutical product of claim 1 comprising by weight of the pharmaceutical product:
(a) colesevelam hydrochloride in an amount of 12.5%;
(b) maltitol solids in an amount in the range of 52-54%;
(c) one or more of: maltodextrin and gum acacia as the bulking agent totaling an amount in the range of 5-15%;
(d) palm oil as the lubricant in an amount in the range of 1.5-6%;
(e) glycerin as the humectant in an amount in the range of 1-3%;
(f) lecithin as the emulsifier in an amount in the range of 1-2%;
(g) a flavoring in an amount in the range of 0.01-6%;
(h) water in an amount in the range of 11.5-12.5%; and
(i) optionally one or more of a powdered sweetener, a coloring, and an antioxidant;
wherein ingredients (a)-(i) total 100%.

13. The chewable pharmaceutical product of claim 1 comprising the colesevelam hydrochloride in an amount of 12.5% by weight.

14. The chewable pharmaceutical product of claim 13 comprising by weight of the pharmaceutical product: colesevelam hydrochloride in an amount of 12.5%; maltitol solids in an amount in the range of 52-54%; water in an amount in the range of 11.5-12.5%; and the balance comprising a bulking, a lubricant, a humectant, an emulsifier, a flavoring, and optionally one or more of a powdered sweetener, a coloring, and an antioxidant.

15. A chewable pharmaceutical product comprising:
a matrix comprising: a binder, a bulking agent, a lubricant, a humectant, an emulsifier, and optionally one or more of a flavoring, a coloring, and an antioxidant, wherein the binder comprises one or more maltitol syrups that are present in the pharmaceutical product in an amount in the range of 60-70% by weight; and
colesevelam hydrochloride, wherein water content of the product is provided only by the one or more maltitol syrups and the colesevelam hydrochloride.

16. A method of delivering colesevelam hydrochloride comprising:
administering the chewable pharmaceutical product of claim 1 to a patient in need of glycemic control or lipid-lowering.

17. The method of claim 16, wherein the chewable pharmaceutical product is ingested once per day.

* * * * *